United States Patent [19]

Allan et al.

[11] Patent Number: 4,769,134
[45] Date of Patent: Sep. 6, 1988

[54] OPEN PATIENT FLUID MANAGEMENT METHOD AND SYSTEM

[75] Inventors: Jonathan M. Allan, Milwaukie; Perry W. Guinn, Oregon City, both of Oreg.

[73] Assignee: C D Medical, Miami Lakes, Fla.

[21] Appl. No.: 808,828

[22] Filed: Dec. 13, 1985

Related U.S. Application Data

[63] Continuation-in-part of Ser. No. 799,923, Nov. 20, 1985, abandoned.

[51] Int. Cl.⁴ .............................................. B01D 13/00
[52] U.S. Cl. ..................................... 210/87; 210/646; 210/321.65; 210/929
[58] Field of Search ...................... 210/929, 87, 321.3, 210/90, 646, 188, 321.65

[56] References Cited

U.S. PATENT DOCUMENTS

| | | | |
|---|---|---|---|
| 3,598,727 | 4/1969 | Willock | 210/90 |
| 3,795,318 | 3/1974 | Crane et al. | 210/321.3 |
| 3,939,069 | 2/1976 | Granger et al. | 210/321.3 |
| 3,946,731 | 2/1983 | Lichtenstein | 210/90 |
| 4,113,614 | 9/1978 | Rollo et al. | 210/22 A |
| 4,172,033 | 10/1977 | Willock | 210/90 |
| 4,202,764 | 5/1980 | Afflerbaugh et al. | 210/22 D |
| 4,209,391 | 6/1980 | Lipps et al. | 210/22 A |
| 4,267,040 | 8/1979 | Fresenuis | 210/23 B |
| 4,267,041 | 5/1981 | Schael | 210/109 |
| 4,366,061 | 12/1982 | Papanek et al. | 210/647 |
| 4,370,983 | 2/1983 | Lichtenstein | 210/929 X |
| 4,477,342 | 10/1984 | Allan et al. | 210/321.3 |
| 4,486,303 | 12/1984 | Brous | 210/929 X |
| 4,530,759 | 7/1985 | Schal | 210/321.2 |

*Primary Examiner*—Frank Spear

[57] ABSTRACT

An open, volumetrically regulated patient fluid management system and method are disclosed. Fresh fluid is metered into a patient fluid exchange unit by a first metering device and spent fluid is drawn out by a pump. A back pressure regulator is provided across the pump to maintain its output pressure at a constant value. To the output of the pump are connected a second metering device and an open drain circuit. The second metering device meters out of the patient fluid exchange unit a predetermined quantity of spent fluid. The open drain circuit drains any fluid pumped by the pump, but not removed by the second metering device, to a drain open to atmospheric pressure. When the dialysis unit is deenergized, fluid in the dialyzer returns rapidly to atmospheric pressure by virtue of the open path through the open drain circuit, pump and back pressure regulator to the dialyzer.

21 Claims, 1 Drawing Sheet

OPEN PATIENT FLUID MANAGEMENT METHOD AND SYSTEM

This application is a continuation-in-part of co-pending application Ser. No. 06/799,923, filed Nov. 20, 1985, now abandoned.

BACKGROUND OF THE INVENTION

The present invention relates to patient fluid management systems, such as hemodialysis and fluid infusion systems and methods for patient fluid management.

Patient fluid management systems typically include a fluid exchange unit, for transferring fluids between a patient and a therapeutic device, and a hydraulic circuit, for controlling the flow of a therapeutic fluid to and from the exchange unit. The fluid exchange unit can assume a variety of forms, of which the dialyzer is the most familiar. Various fluids and fluid components can be transferred across the dialyzer membrane depending, in part, on the design of the associated hydraulic circuitry. It is this hydraulic circuitry with which the present invention is most particularly concerned.

For discussion purposes, the present invention is illustrated in the context of a kidney dialysis unit, although the invention is equally useful in a variety of other applications. In a kidney dialysis unit, the patient's blood is moved through one section of the dialyzer, while a dialysate is passed through the other. The dialysate is a solvent designed to draw certain ionic materials from the blood, through the semipermeable membrane, and into the dialysate. In some systems, the hydraulic circuitry is arranged so that the volume of dialysate passed out of the dialyzer precisely matches the volume passed into the dialyzer. In such systems, no net change occurs in the patient's body fluid volume. In other systems, however, the hydraulic circuitry is arranged so that more fluid may be withdrawn from the dialyzer than is provided. In such "ultrafiltration" systems, this difference reflects a net change in the patient's body fluid volume: a quantity of the patient's body fluid is transferred from the patient, across the membrane and into the used dialysate solution. By this technique, waste water may be removed from patients whose kidney function is seriously impaired.

In some prior art systems, ultrafiltration is effected by inserting a pump in the output line of the dialyzer. One such system is shown in U.S. Pat. No. 3,598,727 to Willock. In this device, the dialysate is routed from the dialyzer to a venturi operated with running water. The water passing through the venturi draws used dialysate from the dialyzer at a rate determined by the water flow. The used dialysate and water mixture flows to a drain.

In the '727 Willock system, the amount of ultrafiltration may be calculated mathematically using the permeability of the dialyzer membrane and the pressure drops between the input and output dialysate ports and the input and output blood ports of the dialyzer. This method, however, is cumbersome. Newer systems have eliminated the need for mathematical calculations by using a volume regulated, rather than a pressure regulated approach.

One such volume regulated system, in which the amount of ultrafiltration is determined by comparing the volume of fluid removed with the volume of fluid supplied, is shown in U.S. Pat. No. 4,172,033 to Willock. In this system, the ratio of fluid volume pumped into the dialyzer to fluid volume pumped out can be adjusted by moving the pivot point about which a lever, connecting the input pump cylinder to the output pump cylinder, pivots. By this adjustment, the amount of fluid withdrawn from, or even added to, the patient can be accurately predetermined.

U.S. Pat. No. 4,267,040 to Fresenuis shows another volumetrically regulated dialysis system wherein equal amounts of dialysate are metered into and out of the dialyzer by a pair of matched pumps. Ultrafiltration may be achieved by connecting an auxiliary withdrawal device, such as a volumetric membrane pump, in parallel with the output pump, between the output of the dialyzer and an ultrafiltrate drain. The rate of operation of such auxiliary pump determines the rate of ultrafiltration.

All of the above volumetrically regulated systems suffer from a variety of drawbacks, of which cost and complexity are among the most important.

A "batch" type of ultrafiltration system is shown in U.S. Pat. No. 3,939,069 to Granger, et al. In a "batch" technique, dialysate is continuously recirculated through the dialyzer. In the Granger, et al. system, ultrafiltration is achieved by an auxiliary peristaltic pump which sucks dialysis liquid or surplus air from the top of a dialysate reservoir. The speed of the pump can be varied to change the rate of ultrafiltration.

The Granger, et al. system is undesirable because the ionic gradient across the membrane is constantly changing, making accurate dialysis difficult. The dialysate also needs to be exchanged periodically with fresh dialysate, thereby reducing the dialysis therapy efficiency.

Accordingly, a need remains for improved patient fluid management systems.

SUMMARY OF THE INVENTION

The present invention provides a simple patient fluid management system.

The present invention also provides an accurate patient fluid management system.

The present invention further provides an open, volumetrically regulated patient fluid management system.

The present invention is an open, volumetrically regulated patient fluid management system and a method of patient fluid management. Fresh fluid is metered into a patient fluid exchange unit by a first metering device. Spent fluid is drawn out from the patient fluid exchange unit by a pump. A regulator is provided across the pump to maintain the pressure at the pump output at a constant value. To the output of the pump are connected a second metering device and an open drain circuit. The second metering device meters out of the patient fluid exchange unit a predetermined quantity of spent fluid. The open drain circuit drains any fluid pumped by the pump, but not removed by the second metering device, to a drain open to atmospheric pressure. The amount of flow through such circuit may be varied by adjusting the regulator device so as to change the pump's output pressure. This flow may be further adjusted by a variable size orifice connected in series with the open drain circuit. Flow through the open drain circuit can be indicated by a rotameter and can be collected in a container. When the dialysis unit is deenergized, the fluid in the dialyzer returns rapidly to atmospheric pressure by virtue of the open path through the open drain circuit and through the combination of the pump and back pressure regulator to the dialyzer.

The foregoing and additional features and advantages of the present invention will be more readily apparent from the following detailed description of a preferred embodiment thereof, which precedes with reference to the accompanying drawings.

DETAILED DESCRIPTION OF PREFERRED EMBODIMENT

Figure 1:
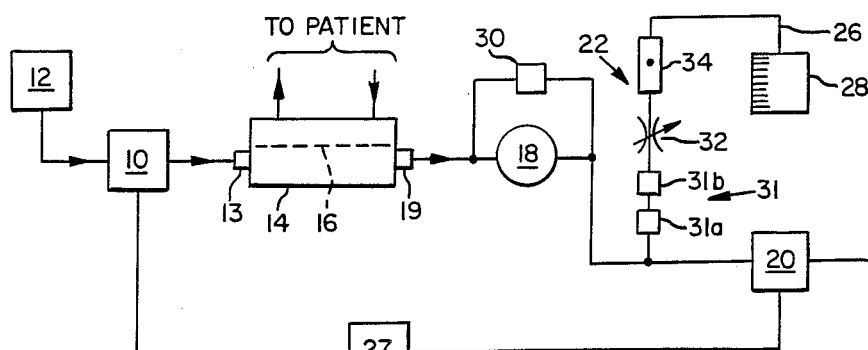
FIG. 1 is a schematic view of a patient fluid management system according to the present invention.

The preferred embodiment of the open dialysis system of the present invention, shown in FIG. 1, includes a first metering device 10 having an input coupled to a source 12 of fluid and an output coupled to an input 13 of a dialysate section of a dialyzer 14. Dialyzer 14 can be any device that permits selective transfer of fluids across a semipermeable barrier. Metering device 10 periodically meters a first volume of fresh fluid into one side of dialyzer 14, the other side being connected to the patient. Inside dialyzer 14 is a semipermeable membrane 16 across which a second volume of filtrate fluid may be transferred between the patient and the dialysis system. A continuously operating pump 18 is connected to the output 19 of dialyzer 14 and withdraws, during each periodic cycle of the first metering device, a third volume of spent fluid from the dialyzer.

Connected to the output of pump 18 is a second metering device 20 and an open drain circuit 22. Second metering device 20 periodically meters a fourth volume of fluid from pump 18 to a first drain 24. Open drain circuit 22 passes the excess, if any, of the third volume of fluid over the fourth volume to a second drain 26. Second drain 26 is open to atmospheric pressure, so that an open system is maintained. That is, second drain 26 allows the fluid in dialyzer 14 to return rapidly to atmospheric pressure when the system is deenergized. In the illustrated embodiment, first drain 24 and second drain 26 are deliberately not connected together so as to avoid reflections in the open drain circuit 22 caused by the metering action of metering device 20.

Figure 5:
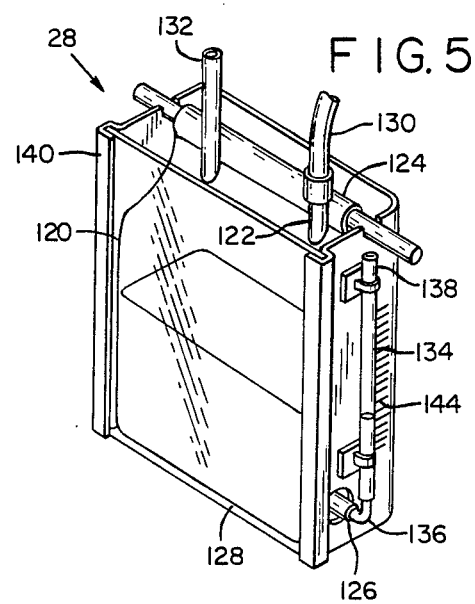
FIG. 5 is a perspective view of a spent fluid collection bag for use with the open drain circuit of the present invention.

Second drain 26 includes a container 28, such as that shown in FIG. 5, for collection of the spent fluid. Calibrations may be added on or adjacent to container 28 to indicate directly and continuously the amount of fluid therein.

In the preferred embodiment, an electronic control circuit 27 and a clock circuit 29 are provided to operate first and second metering devices 10 and 20 periodically and in synchrony. This synchrony produces pulsatile dialysate flow, which is reported to enhance dialyzer performance. Although the metering devices may comprise pumps, they act in a metering, rather than a pumping capacity.

In more detail, pump 18 includes a back pressure regulator 30 for regulating the pressure at the output of the pump. When the pressure at the output of pump 18 is above a desired value, the increased pressure causes a greater amount of fluid to return to the input of the pump, thereby reducing the pressure at its output. If the pressure at the output of pump 18 is below the desired value, a lesser quantity of fluid is returned to the input of the pump, thereby increasing the pressure at its output.

Open drain circuit 22 includes a pressure regulator 31, a flow control device 32 and a flow indicator 34. Regulator 31 regulates the pressure of the liquid passing to flow control 32. Flow control device 32 controls the flow of fluid to second drain 26. Flow indicator 34 indicates directly and continuously the rate of fluid flow to the second drain. Flow control device 32 is desirably a variable size orifice. Flow indicator 34 can comprise a rotameter. The rotameter and the variable size orifice are both simple, inexpensive and reliable devices.

Pressure regulator 31 comprises two serially coupled devices: a coarse pressure regulator 31a and a fine pressure regulator 31b. Coarse pressure regulator 31a serves to regulate the large pressure swings at the output of pump 18 to a smaller magnitude. Fine pressure regulator 31b serves to regulate these small pressure swings to a substantially constant pressure.

Figure 3:
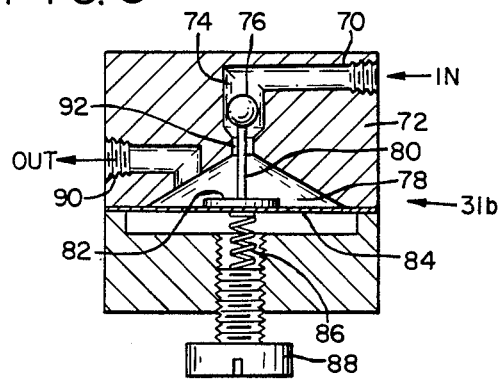
FIG. 3 is a cross-sectional view of a pressure regulator used in the systems of FIGS. 1 and 2.

Fine pressure regulator 31b is illustrated cross-sectionally in FIG. 3. An input port 70 is coupled through a regulator body or housing 72 to a first chamber 74. Within first chamber 74 is a ball 76. Protruding into first chamber 74 from a second chamber 78 is one end of a stem 80, which is in contact with, but not connected to, ball 76. The opposite end of stem 80 is connected to a plate 82 which engages one side of a flexible membrane 84. A compression spring 86 is held in compression against the opposite side of membrane 84 by a bolt 88 threaded in housing 72. An outlet port 90 is coupled to second chamber 78.

In operation, pulsing fluid flowing into input port 70 causes ball 76 to vary the occlusion of the passageway 92 between the first and second chambers, and causes a varying force to be applied against membrane 84 and spring 86 by plate 82. Spring 86 applies a counteracting force against membrane 84 and ball 76 to regulate the occlusion of passageway 92 by ball 76. By this mechanism, the pressure in second chamber 78, and correspondingly the pressure at output port 90, is maintained at a substantially constant value. The output pressure may be varied by positioning bolt 88.

Figure 2:
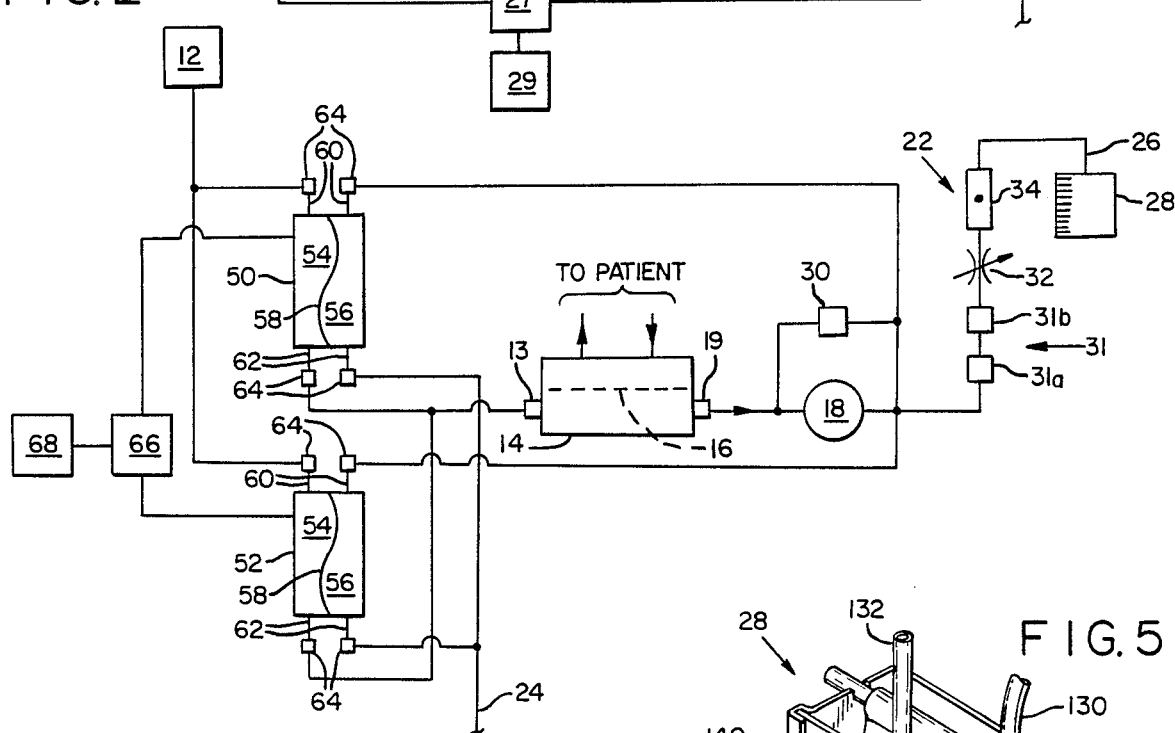
FIG. 2 is a schematic of a patient fluid management system according to the present invention, showing more fully certain features.

In the embodiment of the invention shown in FIG. 2, the first and second metering devices comprise cross-connected, double acting diaphragm pumps 50 and 52. Each pump includes an affluent chamber 54 and an effluent chamber 56 separated by a movable diaphragm 58. These chambers meter dialysate into and out of dialyzer 14. Each such chamber has an input port 60 and an output port 62.

A plurality of controllable valves 64 are connected to the eight chamber ports for controlling the flow of dialysate into or out of the respective chamber. These valves are operable to controllably open and close the ports with which they are associated. The input port 60 of each affluent chamber 54 is coupled through one of valves 64 to a source 12 of fresh fluid. The output port 62 of each affluent chamber 54 is coupled through one of valves 64 to the input 13 of dialyzer 14. The input port 60 of each effluent chamber 56 is coupled through one of valves 64 to the output 19 of dialyzer 14 and the output port 62 of each effluent chamber 56 is coupled through one of the valves 64 to first drain 24.

The illustrated embodiment uses two-way valves on each port of the diaphragm pump, for a total of eight valves. Alternatively, three-way valves (not shown) may be used, a single such valve controlling two ports of the diaphragm pump. In such embodiment, only four valves need be used.

An electronic control system 66, connected to the plurality of valves 64, is provided for configuring the valves into at least two operational states. In the first operational state, the valves are operated to open the following first set of ports: input port 60 of the first pump 50 affluent chamber 54, the output port 62 of the first pump 50 effluent chamber 56, the output port 62 of the second pump 52 affluent chamber 54, and the input port 60 of the second pump 52 effluent chamber 56. The valves are operated to close the remaining, second set of ports in this first operational state. In a second operational state, the valves are operated to close the first set of ports and to open the second set of ports.

The present invention further includes an electronic clock 68 for causing the electronic control system 66 to alternate periodically between the first and second states.

In the two-operational state system with two-way valves, one set of valves is opening while the other set is closing. For a short time, both sets of valves are in a partially open position. This situation can be eliminated by closing one set of valves before opening the other set.

In the preferred embodiment, electronic control system 66 can configure the plurality of valves 64 into such a third operational state in which all of the valves are momentarily closed. During this state, no fluid is moved into or out of dialyzer 14. Clock 68 is operable to cause electronic control system 66 to configure valves 64 in this third operational state during the transition periods between the first and second operational states and between the second and first operational states.

In the illustrated embodiment, metering devices 50, 52 each have the same capacity, but need not have. Since they are cross connected, the volumes metered in and out of the dialyzer will always be equal, even if the metering devices have different capacities. Irregularities in fluid flow due to manufacturing tolerances are thus minimized by the cross connection relationship.

In still other embodiments of the present invention, the open drain circuit need not be on the output side of the dialyzer. For example, in the generic block diagram shown in FIG. 4, the open drain circuit 22 of FIGS. 1 and 2 can be an element of an input circuit 100 or of an output circuit 102, or can even be connected to the dialyzer 104 itself. With reference to this generic system, a first volume (a) of fluid is transferred from a fluid source 106, through a first metering device 108 into input circuit 100. A second volume (b) of fluid is transferred from input circuit 100 to an input port of dialyzer 104. A third volume (c) of fluid is transferred between the patient connected to dialyzer 104 and the dialysate chamber of the dialyzer. This third volume (c) of fluid may be transferred from the patient to the dialyzer, or vice versa. A fourth volume (d) of fluid is transferred from an output port of dialyzer 104 to output circuit 102. A fifth volume (e) of fluid is transferred from output circuit 102 to a drain 110 through a second metering device 112. The excess, if any, of the net fluid volume transferred into the system (the sum of volumes (a) and (c) if fluid is passing from the patient to the dialyzer, or just volume (a) if fluid is passing from the dialyzer to the patient), over the net fluid volume transferred out of the system (the sum of volumes (e) and (c) if fluid is passing from the dialyzer to the patient, or just volume (e) if fluid is passing from the patient to the dialyzer), is allowed to flow through the open drain circuit 110 to atmospheric pressure.

Figure 4:
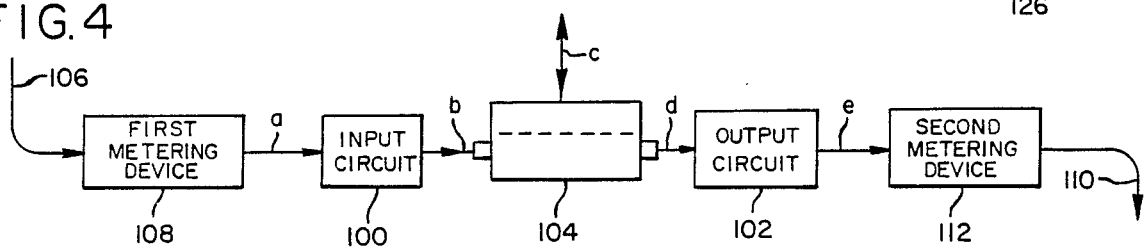
FIG. 4 is a simplified block diagram of the present invention.

With respect to the systems shown in FIGS. 1 and 2, input circuit 100 of FIG. 4 comprises a direct connection between first metering device 108 and dialyzer 104. Output circuit 102 comprises a connection between dialyzer 104 and a pump, a connection between the pump and second metering device 112, and an open drain circuit.

A container 28 suitable for collecting used dialysate or spent fluid from the second drain 26 of the systems shown in FIGS. 1 and 2 is shown in FIG. 5. Container 28 comprises a disposable bag 120 having an inlet port 122 at its top 124 and an output port 126 at its bottom 128. A tube 130 is provided to connect the second drain 26 of the patient fluid management apparatus to bag inlet port 122. A vent 132 maintains the end of tube 130 at atmospheric pressure. A clear sight tube 134 has a first end 136 connected to bag outlet port 126 and a second end 138 open to atmospheric pressure at an elevation above that of the first end. Fluid collecting in the bag thus causes a level of fluid to rise in sight tube 134 to indicate the relative quantity of fluid contained therein.

Bag 120 is adapted to be received in spent fluid container receptacle 140 mounted to the patient fluid management apparatus. Either receptacle 140 or sight tube 134 may be labelled with calibrations 144 so that the quantity of fluid in the bag can be precisely indicated. If calibrations are omitted, a relative quantity of fluid in the bag may still be indicated by reference to clear sight tube 134. Different fluid level resolutions on sight tube 134 may be achieved by varying the capacity of bag 120.

The present invention can be used in a variety of applications other than ultrafiltration. For example, it may be used in sterile fluid infusion or hemodiafiltration processes. When used to infuse fluids into the patient, the quantity of fluid transferred out of the dialyzer is less than that transferred into the dialyzer, with the difference in fluid volume being transferred to the patient. The capacity of the first metering device must in this application be selected to be greater than that of the second metering device, unless an infusion pump is coupled between a fresh fluid source and the dialyzer input circuit. The system may still be maintained in an "open" state, however, by providing the open drain circuit described above. In this application, the open drain circuit would pass to atmospheric pressure the net excess fluid volume, i.e. the excess of the fluid volume transferred into the system (by the first metering pump and by the optional infusion pump), over the fluid volume transferred out of the system (by the second metering pump and by infusion into the patient).

The invention may also be used as a component in a hemodiafiltration system. In such a system, fluids can be removed from the patient by the present invention and replaced externally, such as by an intravenous drip.

The invention may alternatively be configured so that the dialysate does not flow through the dialyzer, but instead is stationary within it. Fluids can then be drawn across the membrane by maintaining the stationary dialysate at a reduced pressure, by proper operation of the pump and the open drain circuit.

Having described and illustrated the principles of our invention in a preferred embodiment and several variations thereof, it should be apparent to those skilled in the art that the invention may be modified in arrangement and detail without departing from such principles. We claim all modifications coming within the scope and spirit of the following claims.

We claim:

1. An open method of patient fluid management utilizing a semipermeable membrane apparatus, said apparatus including a semipermeable membrane device with an input port and an output port, the apparatus further including a first volumetric metering means operable to transfer a fixed volume of fluid from its input to its output per operational cycle, a second volumetric metering means operable to transfer a fixed volume of fluid from its input to its output per operational cycle, an input circuit disposed between the first volumetric metering means and the input port of the membrane device and an output circuit disposed between the output port of the membrane device and the second volumetric metering means, said method comprising the steps of:
operating the first volumetric metering means to transfer a first volume of fresh fluid from a source of fresh fluid into the input circuit;
transferring a second volume of fresh fluid from the input circuit to the membrane device input port;
transferring a third volume of fluid between a patient and the membrane device;
transferring a fourth volume of spent fluid from the output port of the membrane device to the output circuit;
operating the second volumetric metering means to transfer a fifth volume of the spent fluid from the output circuit to a drain; and
continuously allowing the excess, if any, of the net fluid volume transferred into the membrane device, over the net fluid volume transferred out of the membrane device, to flow to an open drain circuit outlet that is open to atmospheric pressure, thereby maintaining an open system.

2. The method of claim 1 which further comprises allowing said excess to flow to the open drain circuit outlet from either said input circuit, said output circuit, or both.

3. The method of claim 1 in which the transferring steps occur substantially simultaneously.

4. The method of claim 1 which further includes controlling the rate of fluid flow to the open drain circuit outlet.

5. The method of claim 1 which further includes indicating directly and continuously the rate of fluid flow to the open drain circuit outlet.

6. The method of claim 1 which further includes collecting said excess fluid from the open drain circuit outlet.

7. The method of claim 6 in which the collecting step includes indicating directly and continuously the amount of the fluid collected.

8. The method of claim 1 in which transferring a fourth volume includes:
pumping the spent fluid from the output port of the membrane device to a designated point; and
regulating the pressure at the designated point by returning a variable amount of the spent fluid from the designated point to the output port.

9. The method of claim 1 in which:
transferring a fourth volume includes pumping the spent fluid through a pump from the output port of the membrane device to a pump output and regulating the pressure at the pump output by returning a controllable amount of the fluid from the pump output to the membrane device output port through a back pressure regulator under the influence of the pressure difference across the pump, and which further includes the steps:
collecting said excess fluid in a container open to atmospheric pressure;
controlling the rate of said excess fluid flow to the container;
indicating directly and continuously the rate of fluid flow to the container; and
indicating directly and continuously the quantity of fluid in the container.

10. The method of claim 1 in which the patient fluid management comprises ultrafiltration, wherein:
the third volume of fluid is transferred from the patient to the membrane device; and
the fourth volume is greater than or equal to the second volume.

11. The ultrafiltration method of claim 10 in which the fifth volume is equal to the first volume.

12. The method of claim 1 in which the patient fluid management comprises fluid infusion, wherein:
the third volume of fluid is transferred from the membrane device to the patient; and
the fourth volume is less than or equal to the second volume.

13. An open patient fluid management system for use with a semipermeable membrane device comprising:
first volumetric metering means having an input coupled to a source of fresh fluid and an output coupled to an input of the membrane device, for metering a first volume of fresh fluid into the membrane device during an operational cycle;
membrane means for transferring a second volume of fluid between the patient and the membrane device during said operational cycle;
pump means having an input coupled to an output of the membrane device for withdrawing a third volume of spent fluid from the membrane device to a pump means output during said operational cycle;
second volumetric metering means having an input coupled to the pump means output and having an output coupled to a first drain, for metering a fourth volume of fluid from the pump means output to the first drain during said operational cycle;
open drain means having an input coupled to the output of the pump means and an output coupled to a second drain open to atmospheric pressure, for passing continuously any excess of the third volume of fluid over the fourth volume to the second drain, whereby an open system is maintained.

14. The system of claim 13 in which the second drain comprises a container and includes means for indicating directly and continuously the amount of fluid in the container.

15. The system of claim 13 in which the open drain means includes flow control means having an input coupled to the output of the pump means and an output coupled to the second drain, for controlling the flow of excess fluid to the second drain.

16. The system of claim 13 in which the open drain means includes a flow indicator means interposed between the output of the pump means and the second drain for indicating directly and continuously the flow of the excess fluid to the second drain.

17. The system of claim 13 in which the pump means includes back pressure regulator means for regulating the pressure at the output of the pump means.

18. The system of claim 13 in which:
the pump means includes a back pressure regulator means for regulating the pressure at the output of the pump means;
the open drain means includes a flow control means for controlling the flow of fluid to the second drain and a flow indicator means for indicating directly and continuously the rate of said flow; and
the second drain includes a container and means for indicating directly and continuously the amount of fluid in the container.

19. The system of claim 18 in which:
the first and second metering means comprise cross connected, double acting diaphragm pumps;
the open drain means includes a pressure regulator;
the flow control means comprises a first variable size orifice; and
the flow indicator means comprises a rotameter.

20. A system for passing fluid through a semipermeable membrane device comprising:
first and second twin chambered pump means, each having an affluent chamber and an effluent chamber separated by a movable diaphragm, each such chamber having an input port and an output port, for metering dialysate into and out of the membrane device;
a plurality of controllable valve means connected to said chamber ports for controlling the flow of dialysate into or out of the respective chamber, said valve means being operable to controllably open and close the ports with which they are associated;
the input port of each affluent chamber being coupled through one of said valve means to a source of fresh fluid; the output port of each affluent chamber being coupled through one of said valve means to an input of the membrane device; the input port of each effluent chamber being coupled through one of said valve means to an output of the membrane device; and the output port of each effluent chamber being coupled through one of said valve means to a spent fluid output circuit;
electronic control means for configuring the plurality of valve means into at least two operational states; in the first operational state the valve means being operated to open the following first set of ports: the input port of the first pump means affluent chamber, the output port of the first pump means effluent chamber, the output port of the second pump means affluent chamber, and the input port of the second pump means effluent chamber, and to close the remaining second set of ports; in the second operational state the valve means being operated to close the first set of ports and to open the second set of ports; and
electronic clock means for causing the electronic control means to alternate periodically between the first and second states.

21. The system of claim 20 in which:
the electronic control means is also capable of configuring the plurality of valve means into a third operational state in which all of the valve means are closed; and
the clock means is operable to cause the electronic control means to configure the valves in said third operational state during a transition period between the first and second operational states and also between the second and first operational states.

* * * * *